(12) United States Patent
Smith

(10) Patent No.: US 7,731,710 B2
(45) Date of Patent: Jun. 8, 2010

(54) SURGICAL WIDE-ANGLE ILLUMINATOR

(75) Inventor: Ronald T. Smith, Newport Coast, CA (US)

(73) Assignee: Alcon, Inc., Hunenberg (CH)

( * ) Notice: Subject to any disclaimer, the term of this patent is extended or adjusted under 35 U.S.C. 154(b) by 847 days.

(21) Appl. No.: 11/590,012

(22) Filed: Oct. 31, 2006

(65) Prior Publication Data
US 2007/0100327 A1 May 3, 2007

Related U.S. Application Data

(60) Provisional application No. 60/731,770, filed on Oct. 31, 2005.

(51) Int. Cl.
A61B 18/18 (2006.01)
(52) U.S. Cl. .............................. 606/16; 606/4; 607/88; 362/558; 362/572
(58) Field of Classification Search ............... 606/2–19; 607/88–95; 362/558, 572
See application file for complete search history.

(56) References Cited

U.S. PATENT DOCUMENTS

| | | | | |
|---|---|---|---|---|
| 4,898,450 | A | * | 2/1990 | Jannson et al. ................. 385/50 |
| 5,196,005 | A | * | 3/1993 | Doiron et al. ................... 606/7 |
| 5,430,620 | A | * | 7/1995 | Li et al. ....................... 362/572 |
| 5,615,673 | A | * | 4/1997 | Berger et al. ................. 600/326 |
| 5,624,438 | A |   | 4/1997 | Turner |
| 5,997,155 | A | * | 12/1999 | Ducharme et al. .......... 362/298 |
| 2005/0075628 | A1 |  | 4/2005 | Cazzini |

OTHER PUBLICATIONS

Roland Winston, Juan Minano, Pablo Benitez, Nonimaging Optics, Dec. 2004, Elsevier Academic Press.

* cited by examiner

Primary Examiner—Henry M Johnson, III
Assistant Examiner—Aisha Hunte
(74) Attorney, Agent, or Firm—Armando Pastrana, Jr.

(57) ABSTRACT

A high-efficiency, wide-angle illumination surgical system is disclosed, one embodiment comprising: a light source for providing a light beam; an optical cable, optically coupled to the light source for receiving and transmitting the light beam; a handpiece, operably coupled to the optical cable; an optical fiber, operably coupled to the handpiece, wherein the optical fiber is optically coupled to the optical cable to receive and transmit the light beam; an optical element, optically coupled to a distal end of the optical fiber, for receiving the light beam and scattering the light beam to illuminate an area, wherein the optical element comprises a compound parabolic concentrator ("CPC") cone; and a cannula, operably coupled to the handpiece, for housing and directing the optical fiber and the optical element. The optical element can be a small-gauge, diffusive optical element comprising a sculpted distal end of the optical fiber or a machined or injection-molded plastic CPC-cone. For example, the optical element can be a 19, 20 or 25 gauge optical element. The CPC-cone optical element angularly spreads the light beam out to a high off-axis angle and emits the light out of the distal end of the cannula with high efficiency.

31 Claims, 4 Drawing Sheets

SURGICAL WIDE-ANGLE ILLUMINATOR

CROSS-REFERENCE TO RELATED APPLICATIONS

This application claims priority under 35 U.S.C. §119 to U.S. Provisional Patent Application No. 60/731,770, filed Oct. 31, 2005, the entire contents of which are incorporated herein by reference.

TECHNICAL FIELD OF THE INVENTION

The present invention relates generally to surgical instrumentation. In particular, the present invention relates to surgical instruments for illuminating an area during eye surgery. Even more particularly, the present invention relates to a compound parabolic concentrator (CPC) cone, wide-angle illuminator for illumination of a surgical field.

BACKGROUND OF THE INVENTION

In ophthalmic surgery, and in particular in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle illuminators can thus illuminate a larger portion of the retina as required by current wide-angle surgical microscope systems. Currently existing wide-angle illuminators, however, display several disadvantages.

One disadvantage of prior art wide-angle illuminators for ophthalmic surgery is a matching of the light refracting index of the vitreous eye fluid to that of the light refracting surface of the lens of the illuminator that comes in contact with the vitreous eye fluid. Contact of the vitreous eye fluid with the light refracting surface of the light spreading lens of such prior art systems results in sub-optimal light refraction due to index switching caused by the vitreous eye fluid. U.S. Pat. No. 5,624,438, entitled "Retinal Wide-Angle Illuminator For Eye Surgery," and issued to R. Scott Turner, provides a system for overcoming the effect of refractive index matching through the use of a high refractive-index step, mediated by the presence of an air-gap. The air-gap is presented between the distal end of an optical fiber and the light refracting surface of the illuminator lens. The light emanating from the optical waveguide (i.e., the optical fiber) will therefore undergo angular dispersion without any index switching that might be caused by contact with the vitreous eye fluid before it passes through the light refracting surface of the illuminator lens.

Another disadvantage of currently available wide-angle illuminators is glare. Glare results when the source of the illumination is small and bright, and the user (e.g., an ophthalmic surgeon) has a direct line of sight to the small bright illumination source. Glare is unwanted stray radiation that provides no useful illumination, and either distracts an observer or obscures an object under observation. Glare can be corrected for in current wide-angle illuminators, but typically only by reducing the total illumination light flux, which reduces the amount of light available for observation by the surgeon. For example, the "bullet probe" manufactured by Alcon Laboratories, Inc., of Fort Worth, Tex., achieves wide-angle illumination by using a bullet-shaped fiber having a surface diffusive finish to scatter light emanating from the distal end of an optical fiber. To reduce glare, the bullet probe can use a geometric shield, which reduces the illumination angle by reducing the overall available light flux.

A further disadvantage of typical prior art wide-angle illuminators is that they do not provide simultaneously both a large illumination angle (angular spread) and high emission efficiency of the light source to illuminate a surgical site.

Therefore, a need exists for a surgical wide-angle illuminator that can reduce or eliminate the problems of associated with prior art wide-angle illuminators, particularly the problem of simultaneously providing both a large angular spread and high emission efficiency of the emitted light.

BRIEF SUMMARY OF THE INVENTION

The embodiments of the high-efficiency wide-angle surgical illuminator for illuminating a surgical field of the present invention substantially meet these needs and others. One embodiment of the present invention is a small-gauge, high-efficiency illumination surgical system comprising: a light source for providing a light beam; an optical cable, optically coupled to the light source for receiving and transmitting the light beam; a handpiece, operably coupled to the optical cable; an optical fiber, operably coupled to the handpiece, wherein the optical fiber is optically coupled to the optical cable to receive and transmit the light beam; an optical element, optically coupled to a distal end of the optical fiber, for receiving the light beam and scattering the light beam to illuminate an area (e.g., a surgical site), wherein the optical element comprises a compound parabolic concentrator ("CPC") cone; and a cannula, operably coupled to the handpiece, for housing and directing the optical fiber and the optical element.

The optical element can be a small-gauge, diffusive optical element comprising a sculpted distal end of the optical fiber or a machined or injection-molded plastic CPC-cone. For example, the optical element can be a 19, 20 or 25 gauge optical element. The CPC-cone optical element angularly spreads the light beam out to a high off-axis angle and emits the light out of the distal end of the cannula with high efficiency. Almost all of the light beam escapes the optical element through the planar distal end face of the CPC-cone.

The cannula, optical element and the handpiece can be fabricated from biocompatible materials. The optical cable can comprise a first optical connector operably coupled to the light source and a second optical connector operably coupled to the handpiece (to optically couple the optical cable to the optical fiber housed within the handpiece and cannula). These connectors can be SMA optical fiber connectors. The optical element, optical fiber and optical cable (i.e., the optical fiber(s) within the optical cable) should be of a compatible gauge so as to transmit the light beam from the light source to the surgical field. For example, all three elements could be of equal gauge.

Another embodiment of the present invention is a small-gauge, wide-angle illuminator, comprising: an optical fiber, operable to be optically coupled to a light source and receive a light beam from the light source and transmit the light beam to illuminate an area; a handpiece, operably coupled to the optical fiber; an optical element, operable to receive the light beam and scatter the light beam to illuminate the area, wherein the optical element comprises a compound parabolic concentrator ("CPC") cone; and a cannula, operably coupled to the handpiece, for housing and directing the optical fiber and the optical element. The area can be a surgical site, such as the retina. The CPC cone can comprise a sculpted distal end of the optical fiber, or a separate machined or injection-molded plastic CPC cone optically coupled to a distal end of the optical fiber.

Other embodiments of the present invention can include a method for wide-angle illumination of a surgical field using a high-efficiency wide-angle illuminator in accordance with the teachings of this invention, and a surgical handpiece embodiment of the wide-angle illuminator of the present invention for use in ophthalmic surgery. Embodiments of this invention can be implemented as a handpiece connected to a cannula or other housing including a fiber optic cable terminating in a diffusive optical element in accordance with the teachings of this invention. Further, embodiments of this invention can be incorporated within a surgical machine or system for use in ophthalmic or other surgery. Other uses for a high-efficiency, wide-angle illuminator designed in accordance with the teachings of this invention will be known to those having skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein.

DETAILED DESCRIPTION OF THE INVENTION

Preferred embodiments of the present invention are illustrated in the FIGURES, like numerals being used to refer to like and corresponding parts of the various drawings.

The various embodiments of the present invention provide for a small gauge (e.g., 19, 20, or 25 gauge) optical fiber based endo-illuminator device for use in surgical procedures, such as in vitreo-retinal/posterior segment surgery. Embodiments of this invention can comprise a handpiece, such as the Alcon-Grieshaber Revolution-DSP™ handpiece sold by Alcon Laboratories, Inc., Fort Worth, Tex., connected to a small gauge cannula (e.g., 19, 20, or 25 gauge). The inner dimension of the cannula can be used to house an optical fiber, which can terminate in a diffusive optical element, integral or separate from the optical fiber, in accordance with the teachings of this invention. Embodiments of the wide-angle illuminator can be configured for use in the general field of ophthalmic surgery. However, it is contemplated and it will be realized by those skilled in the art that the scope of the present invention is not limited to ophthalmology, but may be applied generally to other areas of surgery where wide-angle and/or variable angle illumination may be required.

An embodiment of the high-efficiency, wide-angle illuminator of this invention can comprise an optical fiber, a light diffusive optical element, a stem (cannula) and a handpiece fabricated from biocompatible polymeric materials, such that the invasive portion of the wide-angle illuminator is a disposable surgical item. Unlike the prior art, the embodiments of the high-efficiency, wide-angle illuminator of this invention can provide high optical transmission/high brightness with low optical losses. Embodiments of this invention fabricated from biocompatible polymeric materials can be integrated into a low cost, articulated handpiece mechanism, such that these embodiments can comprise an inexpensive disposable illuminator instrument.

The embodiments of the present invention rely on the edge-ray principle (described by Roland Winston in Non-Imaging Optics, Elsevier Academic Press, 2005). This principle holds that if the highest off-axis angle meridional rays (rays passing through the optical axis of an optical fiber) emitted from the untapered portion of the optical fiber can be focused by a CPC-cone taper onto the distal rim of the cone, then all meridional rays at off-axis angles less than the extreme angle will pass through the distal face of the CPC-cone somewhere within the cone periphery. Tapers designed using this principle display a much better tradeoff between angular beam spread and emission efficiency than is possible with existing wide angle illuminators.

Figure 1:
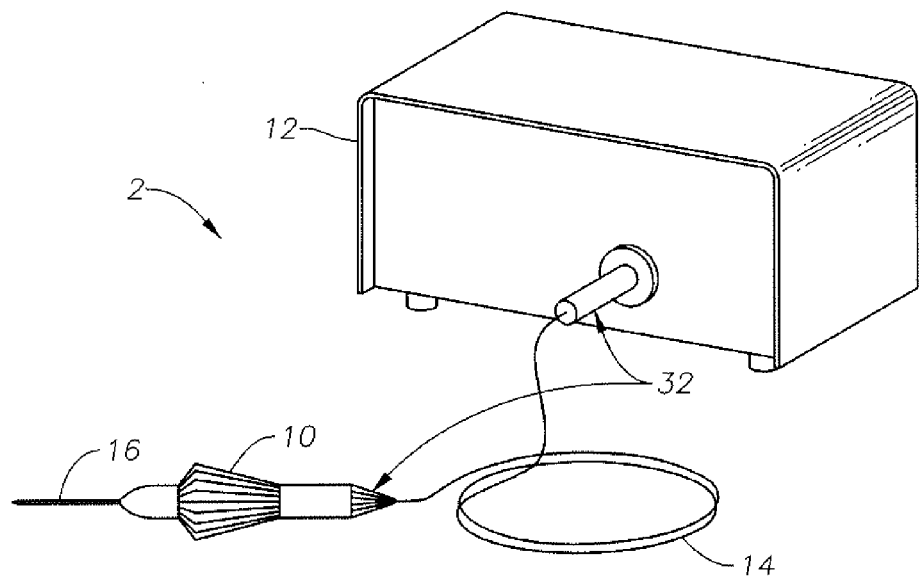
FIG. 1 is a diagrammatic representation of one embodiment of a system for wide-angle illumination in accordance with the teachings of this invention.

FIG. 1 is a diagrammatic representation of a surgical system 2 comprising a handpiece 10 for delivering a beam of light from a light source 12 through cable 14 to a stem 16. Cable 14 can be any gauge fiber optic cable as known in the art, but is preferably a cable having 19, 20, or 25 gauge fiber. Further, cable 14 can comprise a single optical fiber or a plurality of optical fibers optically coupled to light source 12 to receive and transmit the light beam to an optical fiber 22 within stem 16 through handpiece 10. Stem 16 is configured to house the optical fiber 22 and a diffusive optical element 20 at the distal end of stem 16, as is more clearly illustrated in FIGS. 2-4. Diffusive optical element 20 can be integral to or separate from optical fiber 22. Coupling system 32 can comprise an optical fiber connector at each end of cable 14 to optically couple light source 12 to optical fiber 22 within handpiece 10, as discussed more fully below.

Figure 2:
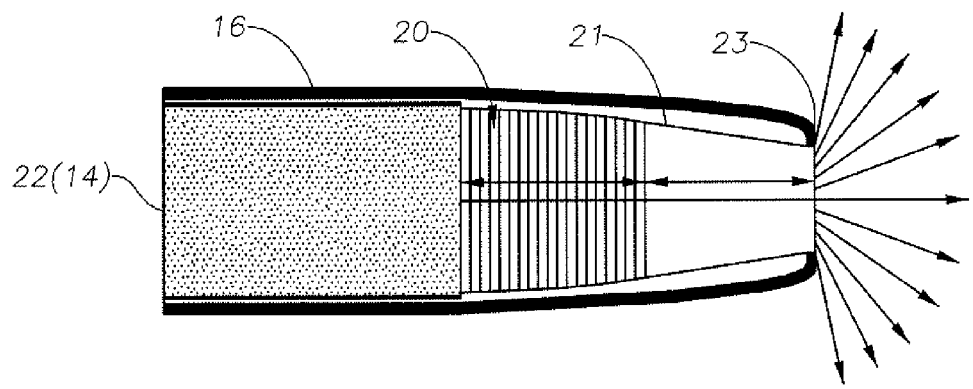
FIG. 2 is a more detailed diagram illustrating an embodiment of a diffusive optical element for wide-angle illumination in accordance with the teachings of this invention.

FIG. 2 is a more detailed diagram illustrating one embodiment of diffusive optical element 20. FIG. 2 provides a magnified view of the distal end of stem 16. Stem 16 is shown housing fiber 22 and optical element 20. Optical element 20 is optically coupled to fiber 22, which is itself optically coupled to fiber optic cable 14. In some embodiments, fiber optic cable 14 can extend through the handpiece 10 and is optically coupled directly to optical element 20. For these embodiments, a separate fiber 22 is not used. In some embodiments, optical element 20 can comprise an integral part of optical fiber 22/14. In such embodiments, the distal end of optical fiber 22/14 is sculpted into a CPC-cone shape that angularly spreads the light out to a high off-axis angle and emits the light from the distal end of optical fiber 22/14 with high efficiency. Alternatively, the flat distal end of an optical fiber 22/14 can be optically bonded to a separate optical element 20, which can comprise an optical grade machined or injection-molded plastic or other polymer.

When implemented within handpiece 10, fiber 22 is of a gauge compatible with the gauge of fiber optic cable 14, such that it can receive and transmit light from fiber optic cable 14. Handpiece 10 can be any surgical handpiece as known in the art, such as the Revolution-DSP™ handpiece sold by Alcon Laboratories, Inc. of Fort Worth, Tex. Light source 12 can be a xenon light source, a halogen light source, or any other light source capable of delivering light through a fiber optic cable. Stem 16 can be a small gauge cannula, preferably within the range of 18 to 30 gauge, as known to those having skill in the art. Stem 16 can be stainless steel or a suitable biocompatible polymer (e.g., PEEK, polyimide, etc.) as known to those having skill in the art.

The fiber optic cable 14 or fiber 22, and/or stem 16 can be operably coupled to the handpiece 10, for example, via an adjusting means 40, as shown in FIG. 6. Adjusting means 40 can comprise, for example, a simple push/pull mechanism as known to those in the art. Light source 12 can be optically coupled to handpiece 10 (i.e., to fiber 22) using, for example, standard SMA (Scale Manufacturers Association) optical fiber connectors at the ends of fiber optic cable 14. This allows for the efficient coupling of light from the light source 12 through fiber optic cable 14 to the handpiece 10 and finally emanating from optical element 20 at the distal end of the stem 16. Light source 12 may comprise filters, as known to those skilled in the art, to reduce the damaging thermal effects of absorbed infrared radiation originating at the light source. The light source 12 filter(s) can be used to selectively illuminate a surgical field with different colors of light, such as to excite a surgical dye.

Figure 3:
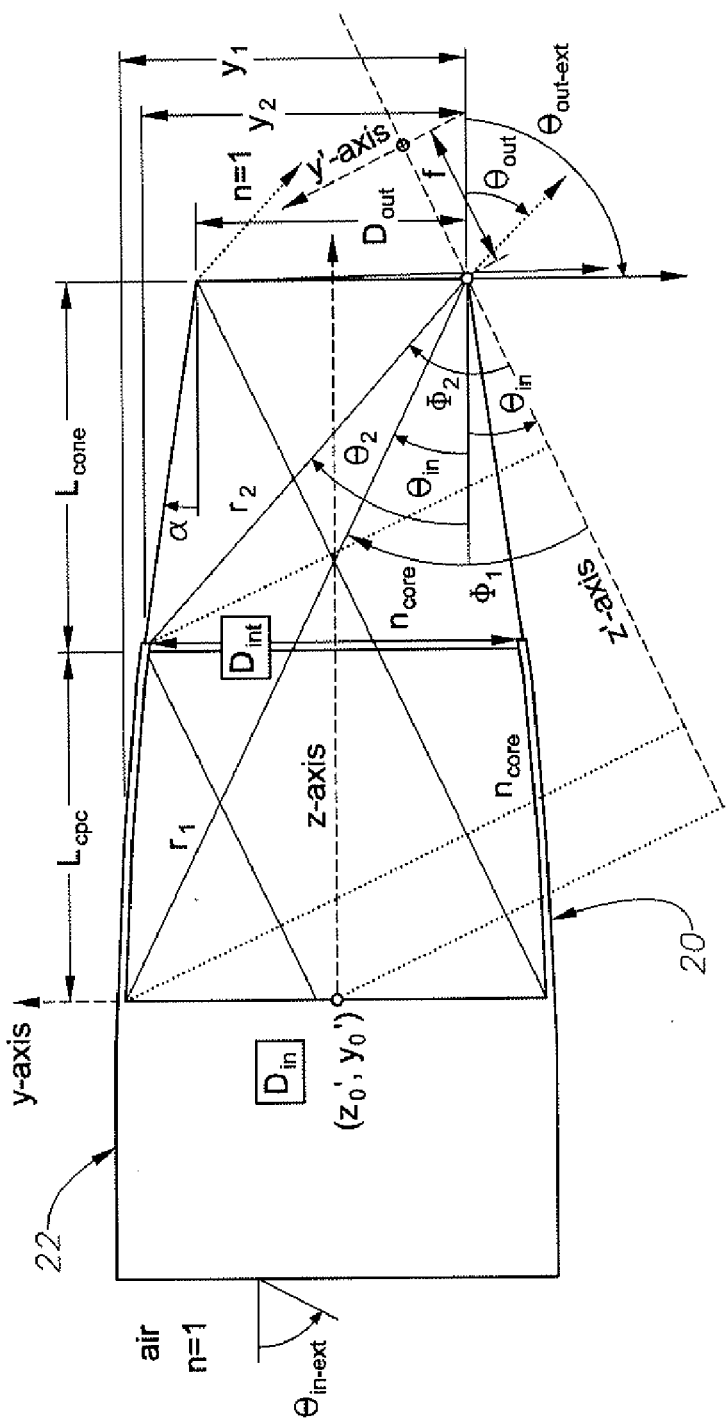
FIG. 3 is a detailed mathematical description of a CPC-cone taper shape of an embodiment of this invention.

FIG. 3 is a diagrammatic representation providing a detailed mathematical description of a CPC-cone taper shape that will accept input light with a maximum half angle of $\theta_{in\text{-}ext}$ (in the fiber core (e.g., fiber 22/14) with refractive index $n_{core}$) and will emit light from the optical element 20 distal end face over an angular spread out to $\theta_{out\text{-}ext}$ half angle (in air). Together with FIG. 4, FIG. 3 illustrates the operation of a CPC-cone concentrator, such as optical element 20 of the present invention.

Figure 4:
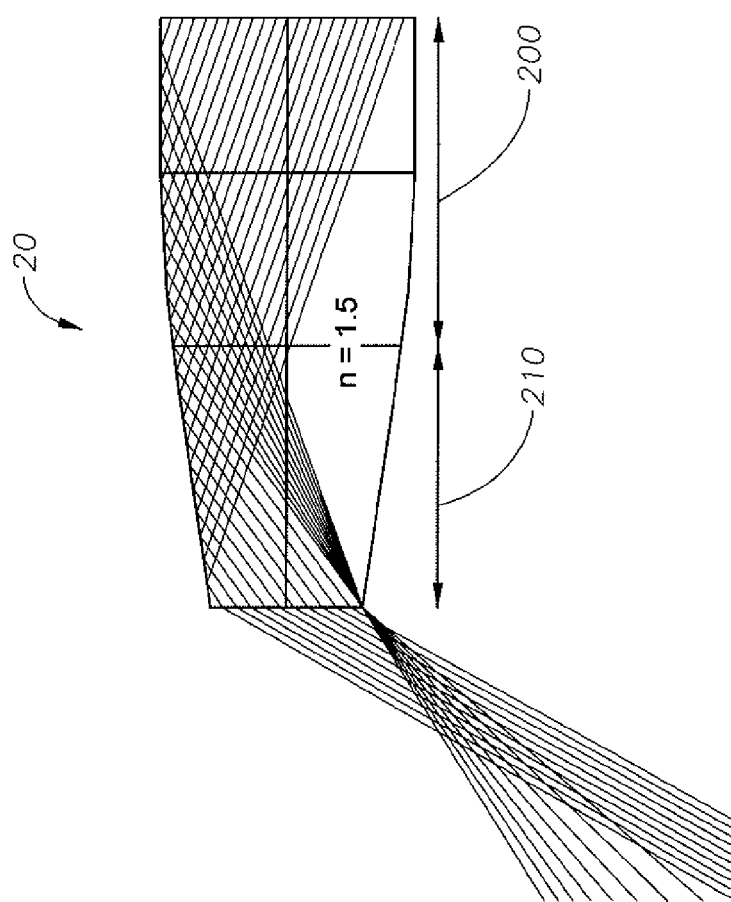
FIG. 4 illustrates the operation of a CPC-cone concentrator optical element in accordance with the teachings of this invention.

An optical element 20 comprising a CPC-cone concentrator as shown in FIG. 4 has the following characteristics:

The extreme off-axis meridional rays at $\theta_{in}=30$ degrees (in air) that strike the CPC region 200 are focused by the CPC to a point on the distal edge of the cone region 210 and pass out of the cone region 210 over a range of angles up to $\theta_{out}=60$ degree in air.

The extreme off-axis meridional rays at $\theta_{in}=30$ degrees that strike the cone region 210 instead of the CPC region 200 are reflected by the cone region 210 and pass through the distal end face of the cone region 210 at an off-axis angle $\theta_{out}=60$ degree in air.

Therefore, 100% of the extreme meridional rays at $\theta_{in}=30$ degrees pass through the CPC-cone optical element 20 and exit through the distal end face. The edge-ray principle holds that if the extreme meridional rays will pass through the distal end face, then the less extreme meridional rays will pass through it as well. Therefore, 100% of the meridional rays with angles less than or equal to 30 degrees will pass through the CPC-cone concentrator 20 of FIG. 4. On the other hand, some of the skew rays (rays that never intersect the optical axis of the concentrator) with incident angles less than or equal to 30 degrees relative to normal, will not pass through the CPC-cone, but will be turned around by multiple TIR (total internal reflection) bounces and will be reflected back up the optical fiber 22/14 in the proximal direction. Therefore, even for an idealized source with uniform intensity out to $\theta_{in}$ and zero intensity past $\theta_{in}$, 100% emission efficiencies are not possible for the 3D case that includes skew rays. Nevertheless, the angular spread vs. emission efficiency tradeoff that is possible with a $\theta_{in}$-$\theta_{out}$ CPC-cone concentrator optical element 20 is much better than is possible with prior art wide angle illuminators.

Using the equations of FIG. 3, the shape of a $\theta_{in}$-$\theta_{out}$ CPC-cone concentrator can be designed for any combination of input and output maximum angles. For a wide angle illuminator in accordance with the present invention, the maximum input angle $\theta_{in}$ can roughly correspond to the arcsine of the optical fiber 22 NA: $\theta_{in}=\arcsin NA_{fiber}$. Thus, for an optical fiber 22 NA=0.5, the input half angle (in air) would be 30 degrees. The output angle can be whatever half angle of the wide angle emitted beam is desired for a particular application. Output half angles as high as 90 degrees in air are possible with the embodiments of the high-efficiency, wide-angle illuminator of this invention.

By optically coupling a CPC-cone shaped optical element 20 to the distal end of an optical fiber 22 (or shaping the distal end of an optical fiber 22 into a CPC-cone shape) and housing the optical assembly within a cannula 16, a high-efficiency wide-angle illuminator of the present invention can be created, one embodiment of which is illustrated in FIG. 2. The CPC-cone optical element 20 can be created either by sculpting the distal end of the optical fiber 22, or by bonding an untapered optical fiber 22's flat distal end to a machined or injection molded plastic CPC-cone optical element 20. The stem (cannula) 16 can be made of steel and is preferably smoothly curved so as to contact the optical element 20 only at the extreme distal end, as shown in FIG. 2. At the point of contact, the optical fiber 22 can be bonded to the stem 16 by means of adhesive 23 to provide mechanical strength and a seal to prevent liquid from the eye from entering into the air gap 21 between the optical element 20 and the stem 16. Preserving air gap 21 is important to ensure that the light rays traveling within the optical path total internally reflect off the side walls of the optical element 20 and exit the distal end of optical element 20 as designed. Stem 16 prevents glare off the distal end of the optical element 20 from scattering back towards the eye lens; however, optical element 20 can also be coupled to stem 16 such that its distal end extends out slightly beyond the distal end of stem 16 with little impact on glare.

The embodiments of the present invention will produce minimal glare, will function in air or in liquid, and can have a much better tradeoff between angular spread and efficiency of the emitted beam than prior art wide-angle illuminators.

Figure 5:
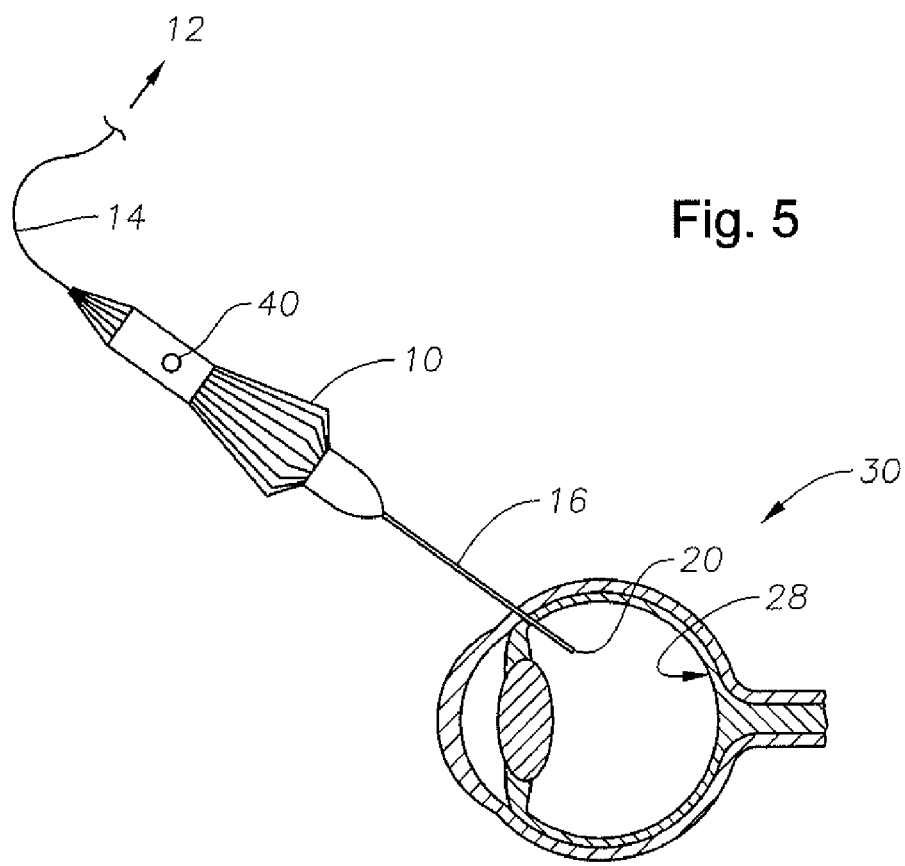
FIG. 5 is a diagram illustrating the use of an embodiment of a wide-angle illuminator of the present invention in ophthalmic surgery.

FIG. 5 illustrates the use of one embodiment of the high-efficiency, wide-angle illuminator of this invention in an ophthalmic surgery. In operation, handpiece 10 delivers a beam of light through stem 16 (via optical fiber 22/14) and through optical element 20 to illuminate a retina 28 of an eye 30. The collimated light delivered through handpiece 10 to the optical assembly 20 is generated by light source 12 and delivered to illuminate the retina 28 by means of fiber optic cable 14 and coupling system 32. Optical element 20 is operable to spread the light beam delivered from light source 12 over as large an area of the retina as, for example, a microscopic wide-angle objective lens permits a surgeon to see.

An advantage of the embodiments of the high-efficiency, wide-angle illuminator of this invention, is that they can provide a more favorable balance when simultaneously having a large angular spread and high emission efficiency than prior art wide-angle illuminators. The embodiments of the present invention can also be implemented as extending, small-gauge wide angle illuminators in accordance with related U.S. application Ser. No. 11/590,392 filed Oct. 31, 2006, the contents of which are hereby fully incorporated by reference.

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide wide-angle and variable illumination of a surgical site.

What is claimed is:

1. A small-gauge, wide-angle illuminator, comprising:
an optical fiber, operable to be optically coupled to a light source and receive a light beam from the light source and transmit the light beam to illuminate an area;
a handpiece, operably coupled to the optical fiber;
an optical element, operable to receive the light beam and scatter the light beam to illuminate the area, wherein the optical element comprises a compound parabolic concentrator ("CPC") cone; and
a cannula, operably coupled to the handpiece, for housing and directing the optical fiber and the optical element; and wherein the CPC cone is optically coupled to a distal end of the optical fiber, and wherein an air gap is disposed between the outer surface of the CPC cone and the inner wall of the cannula.

2. The small-gauge, wide-angle illuminator of claim 1, wherein the CPC cone comprises a sculpted distal end of the optical fiber.

3. The small-gauge, wide-angle illuminator of claim 1, wherein the optical element is optically coupled to a distal end of the optical fiber.

4. The small-gauge, wide-angle illuminator of claim 3, wherein the optical element is machined or injection-molded plastic.

5. The small-gauge, wide-angle illuminator of claim 1, wherein the optical element is a 19, 20 or 25 gauge optical element.

6. The small-gauge, wide-angle illuminator of claim 1, wherein the cannula and the handpiece are fabricated from biocompatible materials.

7. The small-gauge, wide-angle illuminator of claim 1, wherein the optical fiber is optically coupled at a proximal end to an optical cable, wherein the optical cable is operably coupled to the light source to transmit the light beam to the optical fiber, and wherein the optical cable comprises a first optical connector operably coupled to the light source and a second optical connector operably coupled to the handpiece.

8. The small-gauge, wide-angle illuminator of claim 7, wherein the optical cable gauge and the optical fiber gauge are equal.

9. The small-gauge, wide-angle illuminator of claim 7, wherein the optical cable comprises a plurality of optical fibers.

10. The small-gauge, wide-angle illuminator of claim 7, wherein the first and second optical connectors are SMA optical fiber connectors.

11. The small-gauge, wide-angle illuminator of claim 1, further comprising a seal at the distal end between the optical element and the cannula operable to preserve the air gap.

12. The small-gauge, wide-angle illuminator of claim 1, wherein the optical fiber gauge and the optical element gauge are equal.

13. The small-gauge, wide-angle illuminator of claim 1, wherein the light beam comprises a beam of relatively incoherent light.

14. The small-gauge, wide-angle illuminator of claim 1, wherein the light source is a xenon light source.

15. The small-gauge, wide-angle illuminator of claim 1, wherein the handpiece houses at least a portion of the optical fiber.

16. A small-gauge, wide-angle illumination surgical system comprising:
a light source for providing a light beam;
an optical cable, optically coupled to the light source for receiving and transmitting the light beam;
a handpiece, operably coupled to the optical cable;
an optical fiber, operably coupled to the handpiece, wherein the optical fiber is optically coupled to the optical cable to receive and transmit the light beam to illuminate an area;
an optical element, optically coupled to a distal end of the optical fiber, for receiving the light beam and scattering the light beam to illuminate the area, wherein the optical element comprises a compound parabolic concentrator ("CPC") cone; and
a cannula, operably coupled to the handpiece, for housing and directing the optical fiber and the optical element; and wherein an air gap is disposed between the outer surface of the CPC cone and the inner wall of the cannula.

17. The small-gauge, wide-angle illumination surgical system of claim 16, wherein the CPC cone comprises a sculpted distal end of the optical fiber.

18. The small-gauge, wide-angle illumination surgical system of claim 16, wherein the optical element is optically coupled to a distal end of the optical fiber.

19. The small-gauge, wide-angle illumination surgical system of claim 17, wherein the optical element is machined or injection-molded plastic.

20. The small-gauge, wide-angle illumination surgical system of claim 16, wherein the optical element is a 19, 20 or 25 gauge optical element.

21. The small-gauge, wide-angle illumination surgical system of claim 16, wherein the cannula and the handpiece are fabricated from biocompatible materials.

22. The small-gauge, wide-angle illumination surgical system of claim 16, wherein the optical fiber is an integral part of the optical cable.

23. The small-gauge, wide-angle illumination surgical system of claim 16, wherein the optical cable comprises a first optical connector operably coupled to the light source and a second optical connector operably coupled to the handpiece.

24. The small-gauge, wide-angle illumination surgical system of claim 23, wherein the first and the second optical connectors are SMA optical fiber connectors.

25. The small-gauge, wide-angle illumination surgical system of claim 16, wherein the optical cable gauge and the optical fiber gauge are equal.

26. The small-gauge, wide-angle illumination surgical system of claim 16, wherein the optical cable comprises a plurality of optical fibers.

27. The small-gauge, wide-angle illumination surgical system of claim 16, wherein the optical fiber gauge and the optical element gauge are equal.

28. The small-gauge, wide-angle illumination surgical system of claim 16, further comprising a seal at the distal end of the cannula between the optical element and the cannula operable to preserve the air gap.

29. The small-gauge, wide-angle illumination surgical system of claim 16, wherein the light beam comprises a beam of relatively incoherent light.

30. The small-gauge, wide-angle illumination surgical system of claim 16, wherein the light source is a xenon light source.

31. The small-gauge, wide-angle illumination surgical system of claim 16, wherein the handpiece houses at least a portion of the optical fiber.

* * * * *